United States Patent [19]
Shaw et al.

[11] Patent Number: 5,879,366
[45] Date of Patent: Mar. 9, 1999

[54] SELF-EXPANDING DEFECT CLOSURE DEVICE AND METHOD OF MAKING AND USING

[75] Inventors: Edward E. Shaw; Nitin V. Salunke; Gregory T. Mace, all of Flagstaff, Ariz.

[73] Assignee: W.L. Gore & Associates, Inc., Newark, Del.

[21] Appl. No.: 771,718

[22] Filed: Dec. 20, 1996

[51] Int. Cl.[6] .................................................. A61B 17/04
[52] U.S. Cl. .......................... 606/213; 606/151; 606/157; 606/158
[58] Field of Search .............................. 606/78, 151, 157, 606/158, 215, 213

[56] References Cited

U.S. PATENT DOCUMENTS

| | | |
|---|---|---|
| 3,124,136 | 3/1964 | Usher . |
| 3,874,388 | 4/1975 | King et al. . |
| 4,007,743 | 2/1977 | Blake . |
| 4,917,089 | 4/1990 | Sideris ..................................... 606/215 |
| 4,994,077 | 2/1991 | Dobben ........................................ 623/2 |
| 5,108,420 | 4/1992 | Marks ..................................... 606/213 |
| 5,334,217 | 8/1994 | Das ........................................ 606/213 |
| 5,433,727 | 7/1995 | Sideris ..................................... 606/213 |
| 5,536,274 | 7/1996 | Neuss .......................................... 623/1 |
| 5,540,701 | 7/1996 | Sharkey .................................... 606/153 |
| 5,607,465 | 3/1997 | Camilli ......................................... 623/1 |
| 5,626,599 | 5/1997 | Bourne et al. ........................... 606/194 |

FOREIGN PATENT DOCUMENTS

| | | |
|---|---|---|
| 1468511 A1 | 2/1987 | U.S.S.R. . |
| 90/14796 | 12/1990 | WIPO . |
| 94/07560 | 4/1994 | WIPO . |
| 95/27448 | 10/1995 | WIPO . |
| 97/28744 | 8/1997 | WIPO . |

OTHER PUBLICATIONS

Article—A Small Interventional Device to Occlude Persistently Patent Ductus Arteriousus in Neonates: Evaluation in Piglets. *J Am Coll Cardiol 1996*, 28:1024–30.

Primary Examiner—Gary Jackson
Attorney, Agent, or Firm—David J. Johns

[57] ABSTRACT

The present invention relates to a self-expanding device for sealing a defect in a wall, such as a septal defect. The device of the present invention has a fluoropolymer membrane that is supported by an embedded wire structure having elastic properties which is capable of being compressed and inserted in the defect by a catheter and thereafter returning to its memory induced configuration. The device of the present invention can be employed in a variety of applications where a small hole needs to be sealed.

75 Claims, 15 Drawing Sheets

SELF-EXPANDING DEFECT CLOSURE DEVICE AND METHOD OF MAKING AND USING

FIELD OF THE INVENTION

The present invention relates to closure devices, their manufacture and use to occlude a defect in a tissue or muscle of a living animal, such as a human being, or a defect in a wall of a structure, such as a container or filter. More specifically, the present invention relates to a self-expanding closure device having a biocompatible membrane that is supported by a structure having elastic properties, which is capable of being compressed or collapsed and inserted in a tissue defect by a catheter, thoracoscopic or open procedure, and thereafter returned to its memory induced configuration.

BACKGROUND OF THE INVENTION

Defects or apertures have no technological boundaries. A wall defect is generally a hole in the wall of the tissue of a living animal, such as humans, or a hole in the wall of a container, tank, bag filter, or planar filter, tent, inflatable device, etc. In muscles or tissues of living animals, repairs have been accomplished by inserting an occlusion or septal closure device into the aperture or defect. Two such devices include those taught by U.S. Pat. No. 5,334,217 to Das and U.S. Pat. No. 5,108,420 to Marks.

The Das patent describes a septal defect closure device, its use and method of assembly, where individual disks of a thin flexible material are supported by a super-elastic material and are used to occlude a wall defect. The disks are conjointly attached to one another at the center of the disk. The thin flexible material used in the Das patent can include nylon, polyester, polypropylene and polytetrafluoroethylene (PTFE) polymers. The super-elastic material is a NiTi alloy, such as nitinol.

The super-elastic material of the Das patent is formed into a frame having several legs and can assume a variety of geometrical configurations, such as triangles, hexagons, circles, stars, etc. A membrane is wrapped around the legs of the frame. The loops between adjacent legs bias the legs outwardly, to form a concave membrane surface, which is maintained in a highly tensioned fashion.

The Marks patent describes an occlusion device that can be transported via a catheter in a compressed state. Once through the aperture to be occluded, the device is released and wires supporting two membranes are positioned on each side of the aperture. A domed or umbrella shaped configuration is formed and the support wires urge the membranes towards one another and the wall where the aperture is located.

These prior art devices have numerous drawbacks. The support frames of the Das patent include resilient wire loops where leg ends of the frame meet and are attached to one another. The loops generally extend beyond the periphery of the membrane and can irritate or damage adjacent muscle or tissue.

Similarly, the exposed wires of the Marks device act as an irritant to tissue or muscle adjacent the aperture or septum. Here the bare sharp ends of the wire structure can further cause tissue erosion.

The Das and Marks patent devices use a membrane of conventional thickness that when folded over a wire adds undesired thickness to the device. Additionally, the patents rely on peripheral membrane support which leaves the central occlusion covering portion of the membrane vulnerable.

In the Das patent design, each leg is provided with a bend at the middle of its length. This bend can add a tendency to the device to fold when the frame is sitting against a very flexible tissue and the membrane is pressurized by the blood. This may be the potential mechanism of failure as reported by Agarwal, et al. (1996). Agarwal, S. K., Ghosh, P. K. and Mittal, P. K., Failure of Devices Used for Closure of Atrial Septal Defects: Mechanisms and Management, *The Journal of Thoracic and Cardiovascular Surgery*, Vol. 112, No. 1, 1996.

Thus, in view of the above, a need exists for a closure device that eliminates or significantly minimizes the traumatizing effect of existing closure devices. Further, a need exists for a device which is stable under physiological loading conditions when situated against the anatomical tissue structure. A need also exists for a defect closure device that is collapsible or compressible so that it may fit into a 9F (9 French), preferably 5F (5 French) or smaller catheter for deployment in a defect.

A need also exists for a closure device that is able to occlude or close wall defects in structures such as containers, tanks, tents, inflatable devices or filters without removing the structure from its environment of use. The present invention can meet these needs.

SUMMARY OF THE INVENTION

The present invention provides a self-expanding defect closure device that overcomes the many drawbacks and disadvantages of prior devices. The devices of the present invention rely on memory induced support structures having curved outer surfaces that minimize tissue erosion. These structures facilitate repair of septal defects. Also, these structures facilitate repair of containers/filters without their removal from their environments of use. The device of the present invention can also be used with adhesives to repair the walls of tents, fabrics, inflatable devices, etc.

The structures of the present invention radially and circumferentially support a membrane, providing greater central support to the membrane. Thin membranes are laminated together and embed a memory induced elastic wire structure, preferably a super-elastic wire, to reduce the collapsed dimensions of the closure device. Thinner membranes are possible because the preferred thin ply expanded polytetrafluoroethylene (ePTFE) films are cross-laminated to increase membrane strength and maintain a desired microstructure.

The support structure may have a star or helical geometrical configuration. The self-expanding defect closure device of the present invention can be readily deployed by a 9F, preferably 5F, or smaller catheter or thoracoscopic instrument or open procedural tools.

An aspect of the present invention is to provide a closure device having one or two discrete sections where each section has a smoothly curved outer periphery and is formed from a single elastic element.

It is a purpose of the present invention to provide a self-expanding closure device that eliminates or minimizes trauma to existing muscles or tissues surrounding a defect to be occluded.

It is another purpose of the present invention to prepare a closure device by forming a wire structure into a desired configuration and inducing memory of that configuration into the wire, and laminating the wire structure so as to be embedded in the membrane.

It is another aspect of the present invention to manufacture a closure device. Thus it is a purpose of the present invention to manufacture a device by using cross ply laminated ePTFE films by: providing a first cross-ply membrane portion; locating an elastic wire on an upper surface of said first membrane portion; locating a second cross-ply membrane portion on an exposed surface of said wire and in contact with said upper surface of said first membrane portion; and affixing said first and second membrane portions to one another to embed said wire therebetween.

It is another purpose to manufacture a closure device by using cross ply laminated ePTFE films by: providing a cross laminated membrane; locating a heat resistant tube on said membrane; folding and laminating said membrane about said heat resistant tube; inserting an elastic wire into said heat resistant tube; and removing said heat resistant tube and heating said membrane to embed said elastic wire.

It is a further purpose of the present invention to deploy the subject closure devices in walls of containers or filters by providing a delivery tube; compressing and inserting the device into the delivery tube; deploying the compressed device in a defect; and inserting and releasing the device in the wall defect.

Another aspect of the present invention is to insert the closure device in a 9F, preferably 5F, or smaller catheter and deploy that device in a wall defect in a living animal.

These and other aspects and advantages will become more apparent when considered with the following detailed description, drawings and appended claims.

BRIEF DESCRIPTION OF THE DRAWINGS

FIG. 6 (B) shows a side view of a closure device, as the device is being collapsed.

FIG. 6 (C) shows a side view of a closure device, in the fully collapsed or small diameter state.

FIG. 9 (B) shows the heat-treated, memory induced helix shaped wire structure of the present invention, with the thermoplastic bonding agent coating the wire.

FIG. 9 (C) shows the cross section of the helical wire, with the thermoplastic bonding agent coating the wire.

DETAILED DESCRIPTION OF THE INVENTION

Figure 1:
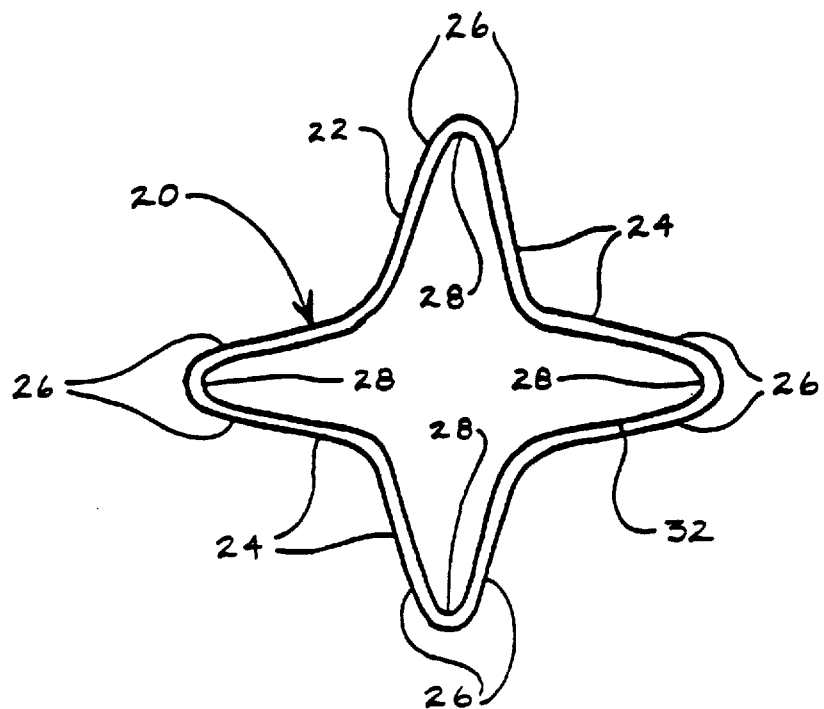
FIG. 1 shows the heat-treated, memory induced star shaped wire structure of the present invention.

The defect closure devices of the present invention are composite assemblies of support structures and membranes, preferably biocompatible membranes. The biocompatible membranes, such as expanded polytetrafluoroethylene (ePTFE), block the defect, for example a septal defect, in the living animal and occlude the blood flow. This device can also be used to repair a variety of wall defects, either by remote or direct deployment.

A wall defect can be remotely repaired in a fluid containing vessel without draining the fluid. Other wall defects in contact with hazardous materials or environments can be remotely repaired. In addition, those defects where access is limited due to confined spaces or submersion, can also be remotely repaired. Direct deployment can be used to repair wall defects in those cases where access is non-restricted or limited by the immediate environment.

The supporting wire structures that are used in the devices according to the present invention have elastic properties which allow for them to be collapsed for catheter based delivery or thoracoscopic delivery, and self-expand to a "memory" induced configuration once positioned in a wall defect. The elastic wire could be a spring wire, or a shape memory NiTi alloy wire or a super-elastic NiTi alloy wire. Upon deployment, the wire structure resumes its deployed shape without any permanent deformation.

The supporting structures of the present invention are formed from elastic wire materials that have diameters between 0.127 and 0.381 mm. In one embodiment of the present invention the wire is about 0.203 mm in diameter and formed from nitinol.

The membrane that is used in the defect closure devices to occlude the flow of blood, can be manufactured from DACRON® polyester, polyethylene, polypropylene, fluoropolymers, polyurethane foamed films, silicone, nylon, silk, thin sheets of super-elastic materials, woven materials, polyethylene terephthalate (PET), pericardium tissue or any other biocompatible material. In one embodiment of the present invention, the membrane material is a fluoropolymer, in particular, expanded polytetrafluoroethylene (ePTFE) having a node-fibril structure. The membrane used in the present invention is manufactured from thin films of ePTFE that are each approximately 0.0025 to 0.025 mm thick. Thus, the films could be 0.0025, 0.0050, 0.0075, 0.0100, 0.0125, 0.0150, 0.175, 0.0200, 0.0225 and 0.025 mm thick.

From 1 to about 200 plys (layers) of ePTFE film are stacked up and laminated to one another to obtain a membrane with the desired mechanical and structural properties. An even number of layers are preferably stacked together (e.g., 2, 4, 6, 8, 10, etc.), with approximately 2 to 20 layers being desirable. Cross-lamination occurs by placing superimposed sheets on one another such that the film drawing direction, or stretching direction, of each sheet is angularly offset by angles between 0 degrees and 180 degrees from adjacent layers or plies. Because the base ePTFE is thin, as thin as 0.0025 mm thick, superimposed films can be rotated relative to one another to improve the mechanical properties of the membrane. In one embodiment of the present invention the membrane is manufactured by laminating 8 plies of ePTFE film, each film ply being 0.0125 mm thick. In another embodiment of the present invention the membrane is manufactured by laminating 4 plies of ePTFE film, each film ply being 0.0125 mm thick. The laminated ePTFE sheets are then sintered together at temperatures of about 370° C., under vacuum to adhere the film layers to one another. The resultant 8 ply laminate structure is typically 0.0375 mm thick.

The invention will now be described by reference to the figures and non-limiting embodiments. As shown in FIG. 1, a star shaped wire frame 20 for a defect closure device, is prepared from a super-elastic wire material 22. A wire 22 of nitinol is fixtured in a jig (not shown) into a shape of a star 20. Star 20 has four arms 24, although different arm configurations may be employed, such as providing more arms (e.g., 5, 6, 7, 8, etc.). Each star 20 is preferably formed from a single wire that is configured to be star shaped, although multiple wires may be used. The star 20 includes eight legs 26 which terminate into four curved arcuate ends 28. The arcuate portion 28 extends over an angle that is less than 360°, and is connected to the distal ends of legs 26.

Figures 6A, 6B, 6C:
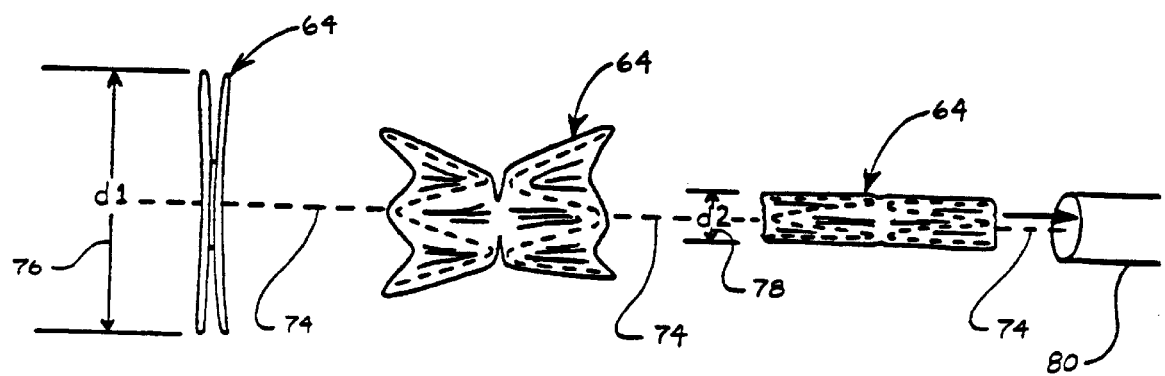
FIG. 6 (A) shows a side view of a closure device, in the deployed or large diameter state.

The star shaped wire 20 is constrained in a jig (not shown) and the combination is placed into an oven, heated for at least two minutes, up to about one-half hour, at about 400° to 600° C., e.g., 500° C. The star shaped wire 20 is cooled by air, water or any other means, and removed from the restraining jig. As the result of the 500° C., 30 minute heat treatment, the nitinol wire 22 obtains a memory induced configuration, which in this case is the shape of a star. Therefor the star shaped wire 20 exhibits super-elastic properties, which act to return the wire to the star shape even after extreme deformation, such as that shown in FIGS. 6(A)–6(C).

Figure 2:
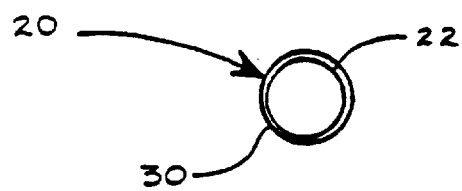
FIG. 2 shows a cross section of the wire in FIG. 1, with the thermoplastic bonding material coating the wire.

As shown in FIG. 2, the cross section of the star shaped wire 20 is coated with a bonding agent 30, for example fluoroethylene polymer (FEP) or other suitable polymer. A close tolerance FEP tube is slipped over the star shaped wire 20, so that the ends of the FEP tube are offset from the wire termination point 32 (FIG. 1). The FEP 30 will then be heated and adhered to the wire 22 during subsequent processing. The FEP coating can also be applied by dipping, spraying, laminating between sheets, or any other means. The two ends of the formed wire are attached together at the termination point 32 in FIG. 1, by welding, by crimping a sleeve onto the wire ends, or any other means.

Figure 3:
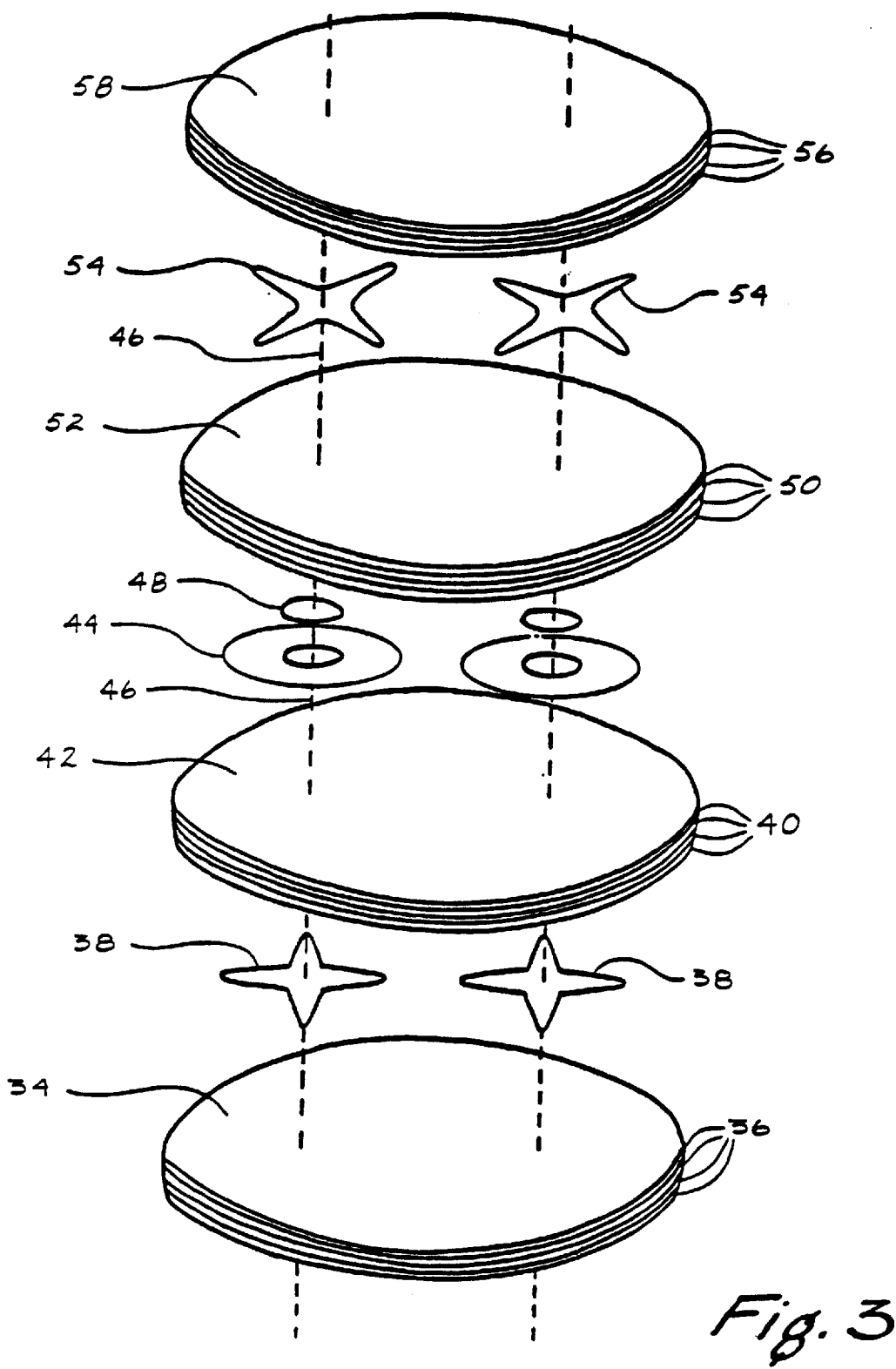
FIG. 3 shows an exploded assembly view of a complete laminate structure for a star shaped closure device where two complete devices are shown, both being fabricated together.

FIG. 3 shows an exploded assembly view of the closure device according to the present invention. A four ply laminate 34 is prepared from four film layers (plies) of ePTFE 36. The film layers 36 are placed onto a porous vacuum chuck (not shown) with each film layer 36 being rotated 90 degrees relative to one another. The four ply laminate 34 can be disk shaped, but could be any other shape.

One or more FEP coated star shaped wire structures 38 are placed onto the four ply laminate 34. Four additional layers of ePTFE film 40, rotated 90 degrees relative to each other, are placed onto the assembly, forming a second four ply laminate structure 42, with the FEP coated wire structures 38 embedded between the two four ply laminates 34 and 42.

A Kapton or other high temperature plastic ring 44 is aligned over the center axis 46 of each star shaped embedded wire 38. A disk of FEP 48 or other suitable bonding polymer is placed into the center of each ring 44. The FEP disk 48 is sized to fit within the central opening of the ring 44. The ring is sized such that the perimeter is larger than the star shaped wire 38.

Four additional film layers of ePTFE 50, rotated 90 degrees relative to each other, are placed onto the assembly, forming a third four ply laminate 52. A second pair of FEP coated star shaped wire structures 54 are aligned to the central axis 46 and rotated 45 degrees relative to the first embedded star shaped structures 38, and placed onto the third four ply laminate 52. Four additional film layers of ePTFE 56, rotated 90 degrees relative to each other, are placed onto the assembly, forming a fourth four ply laminate 58, with the second FEP coated wire structures 54 embedded between the third four ply laminate 52 and fourth four ply laminate 58.

This entire assembly is then covered with a sheet of Kapton or other high temperature plastic (not shown), and placed into a sintering press (not shown). The sintering press constrains the edges of the laminate assembly from contracting and applies vacuum through the porous vacuum chuck to the assembly. Sintering is conducted at temperatures of about 370° C. for a period of several minutes, e.g. 15 minutes, up to several hours. The sintered assembly is cooled and the Kapton sheet is removed and discarded.

Figure 4:
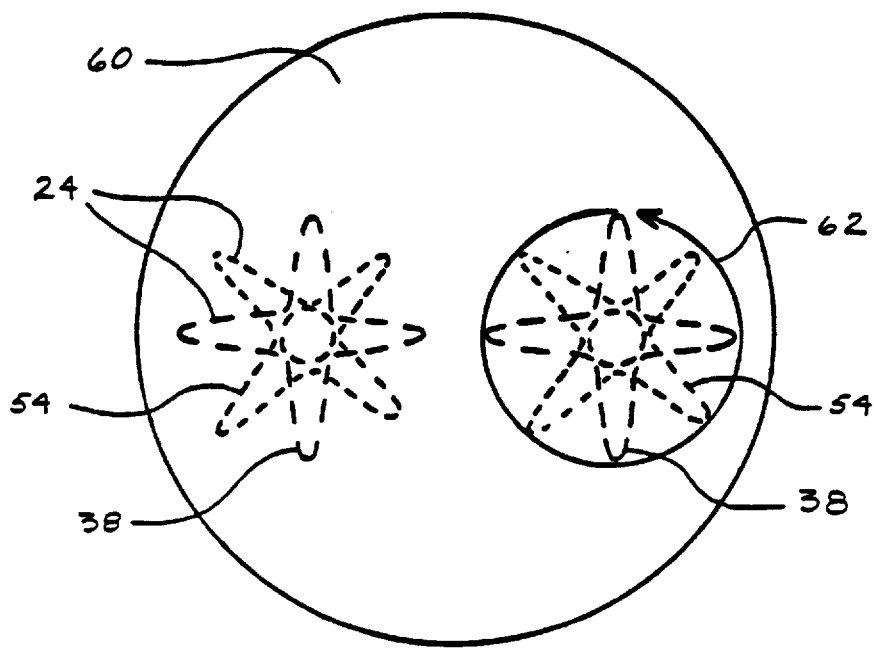
FIG. 4 shows the final laminate sheet and cutting pattern, containing two star shaped closure devices.

As shown in FIG. 4, the embedded star shaped wire structures 38 and 54 are then cut out of the laminated assembly 60 by laser, steel rule die, or any other means, per the cut pattern 62. The arms 24 of stars 38 and 54 radially support the laminated structure in a "relaxed" manner. In other words the laminated structure is not placed under tension by the arms 24 of star 38 and 54, when in the uncompressed or deployed state. The rings 44 (FIG. 3) are removed after the cutting operation.

Figure 5:
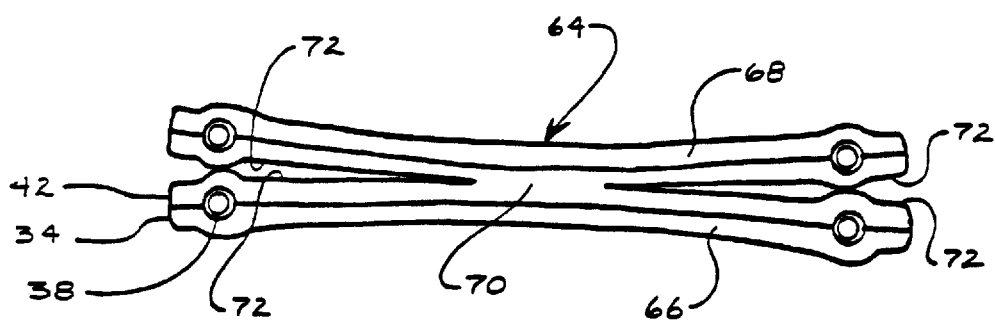
FIG. 5 shows a cross sectional view of a final closure device, detailing the central attachment point between the two membranes.

FIG. 5 shows a cross sectional view of the final closure device 64. Two of the four ply laminate structures 34 and 42 have been sintered together, embedding the FEP coated wire 38 to form a membrane 66. As previously described, the completed device includes a second identical membrane 68. The attachment point 70 between the two membranes is formed by the bonding polymer (e.g., FEP) 48 (FIG. 3), melting and reflowing during the sintering process. This attachment can also be accomplished by suturing, ultrasonic welding, or any other means of attaching the two membranes together. The non-attached surfaces 72 between the two membranes 66 and 68, are a result of the ring 44 (FIG. 3), which prevented complete membrane to membrane attachment during the sintering process.

FIG. 6 (A) shows a side view of a closure device 64, with a longitudinal axis 74, in the deployed or large diameter state 76 having a diameter $d_1$.

FIG. 6 (B) shows a side view of a closure device 64, with a longitudinal axis 74, as the device is being collapsed.

FIG. 6 (C) shows a side view of a closure device 64, with a longitudinal axis 74, in the fully collapsed or small diameter state 78 having a diameter $d_2$, where $d_2$ is less than $d_1$, the ratio of $d_1:d_2$ being less than about 50:1, depending on the final deployed diameter $d_1$ of the device. The ratio of $d_1:d_2$ should be between about 5:1 and about 50:1, with a ratio of about 10:1 to about 50:1 being preferred. Once in the collapsed state, the device can be inserted along the longitudinal axis 74 into a delivery tube 80.

Figure 7A:
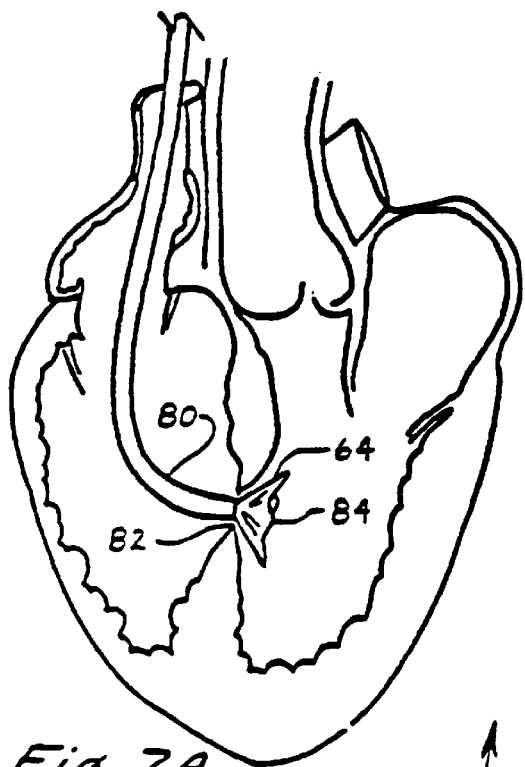
FIGS. 7 (A)–(C) show a star shaped defect closure device according to the present invention being positioned and deployed in a heart defect.
Figure 7B:
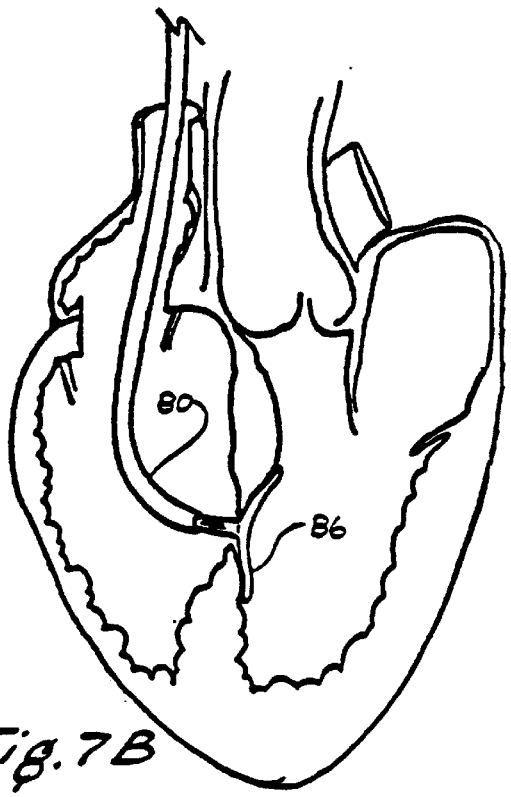
Figure 7C:
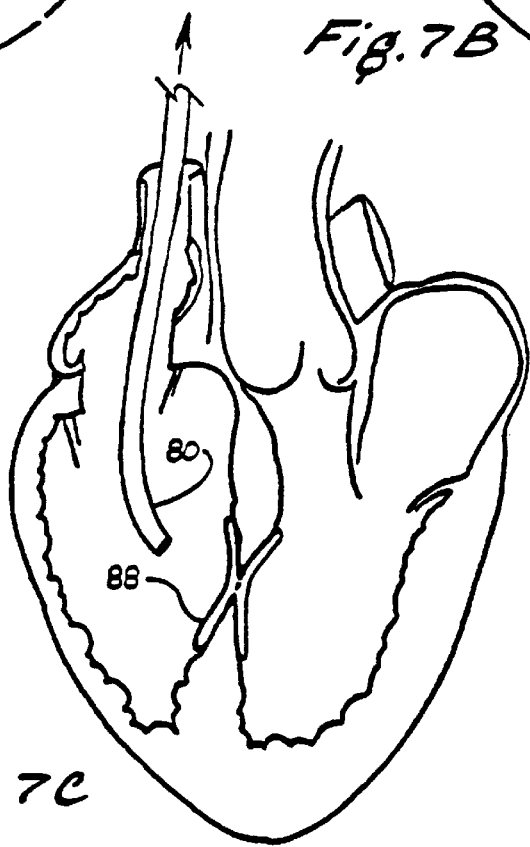
Figure 8:
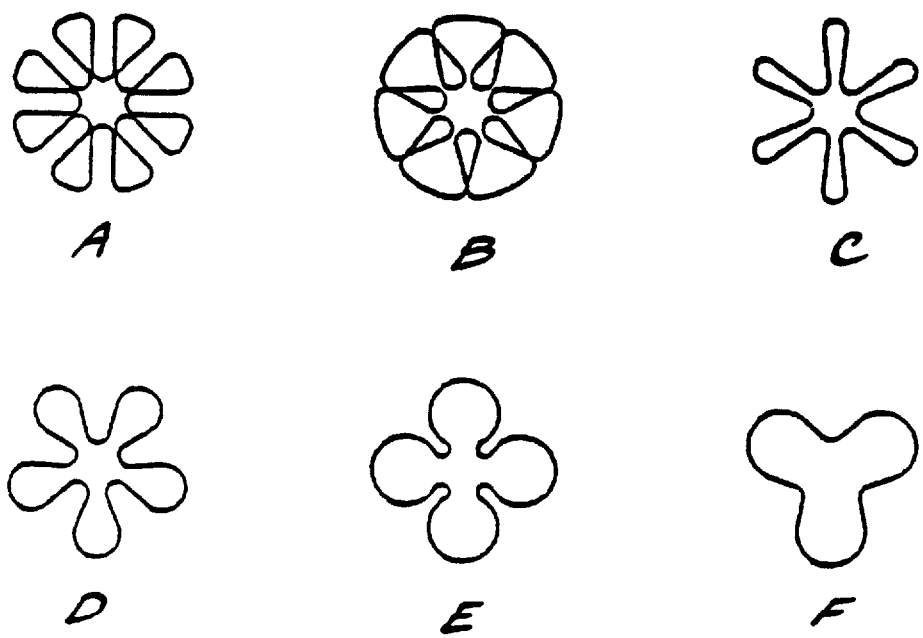
FIGS. 8 (A)–(F) show other configurations of generally star shaped, memory induced wire structures of the present invention.

FIGS. 7 (A)–(C) show the deployment of the star closure device 64. A catheter or delivery tube 80 is loaded with closure device 64 and deployed in a defect 82. As seen in FIG. 7(A), the distal side of the star device 84 expands when released from the catheter 80. As shown in FIG. 7(B), the distal side of the star device assumes its memory induced shape 86, which approximates $d_1$ of FIG. 6(A) 76. As shown in FIG. 7(C), as the catheter 80 is further withdrawn, the proximal side of the device 88 is deployed, which also assumes its memory induced position.

FIGS. 8(A)–(F) show other configurations of star wire structures. The fabrication of a closure device using one of these alternate star configurations is similar to the process used in the initial star device. The number of laminate layers can be varied to achieve the desired thickness and mechanical properties, and the cutting patterns adjusted to produce the desired deployed diameter or shape.

Figure 9A:
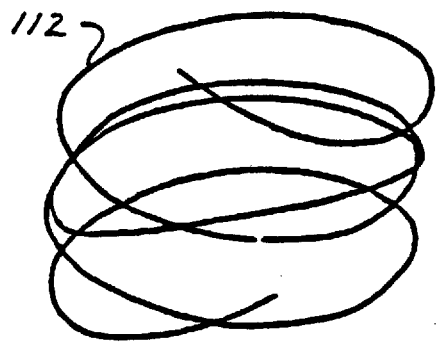
FIG. 9 (A) shows the heat-treated, memory induced helix shaped wire structure of the present invention.

An alternate embodiment for closing an aperture according to the present invention is the helical design. As shown in FIG. 9(A), nitinol wire 112, is placed in a constraining jig (not shown) and wound into the desired helical shape. This coiled, helically shaped wire, while being restrained in the jig (not shown), is placed in a heat treating oven and is subjected to the same "memory" inducing treatment as described before. Upon cooling and/or quenching, the coiled nitinol wire exhibits super-elastic properties which act to return the wire to the coiled, i.e., helical shape, even after extreme deformation, such as extending the wire into a linear configuration.

Figure 9B:
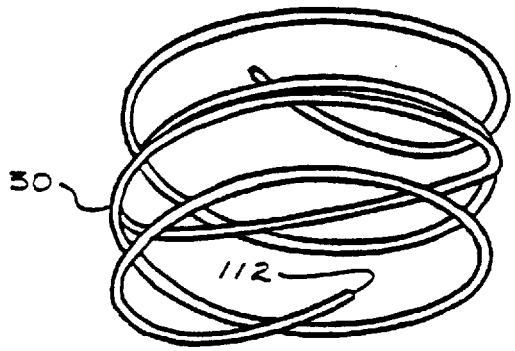
Figure 9C:
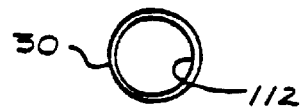

As shown in FIG. 9(B), the helical shaped wire 112 is coated with a bonding agent 30, for example a fluoroethylene polymer (FEP) or other suitable polymer. A close tolerance FEP tube 30 is slipped over the helical shaped wire 112. The FEP tube 30 is then heated and adhered to the wire 112 during subsequent processing. The FEP coating can also be applied by dipping, spraying, laminating between sheets, or any other means. FIG. 9(C) shows a cross section of the wire 112 coated with polymer 30.

Figure 10A:
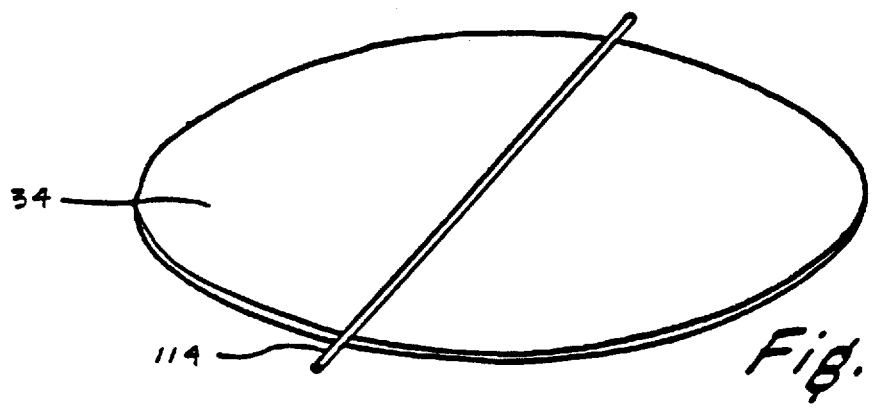
FIGS. 10 (A)–(C) show a four ply laminate being folded over a heat resistant stainless steel tube during the helical device fabrication process.

FIG. 10(A) shows a four ply laminate 34 prepared from four film layers (plies) of ePTFE. The film layers are placed onto a porous vacuum chuck (not shown) with each film layer being rotated 90 degrees relative to one another. The four ply laminate 34 can be disk shaped or any other shape. A high temperature tube 114 is placed on the center line of the four ply laminate 34.

Figure 10B:
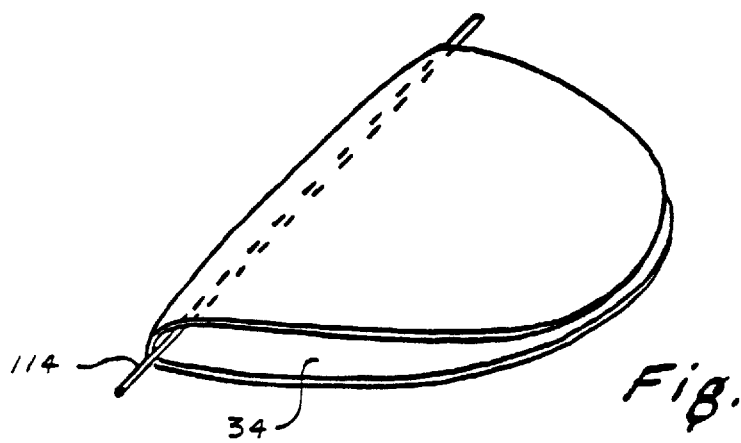

FIG. 10(B) shows the four ply laminate 34 being folded over the high temperature tube 114, forming a folded laminate which surrounds the tube.

Figure 10C:
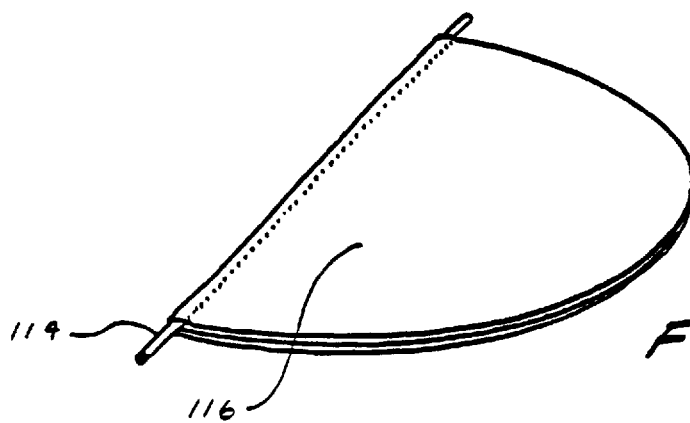

FIG. 10(C) shows the folded laminate. Since the four ply laminate has been folded once, the tube 114 is now embedded within an eight ply laminate, or membrane 116. This laminate assembly, with the embedded tube, is capped with a Kapton sheet and placed into a sintering press. As discussed above, the edges of the laminate are constrained, vacuum is applied to the assembly through the porous chuck, and the assembly heated to sintering temperatures. The temperature and time for the sintering process is the same as that described above for the star shaped configuration. The sintered assembly is cooled and the Kapton sheet is removed and discarded.

Figure 11:
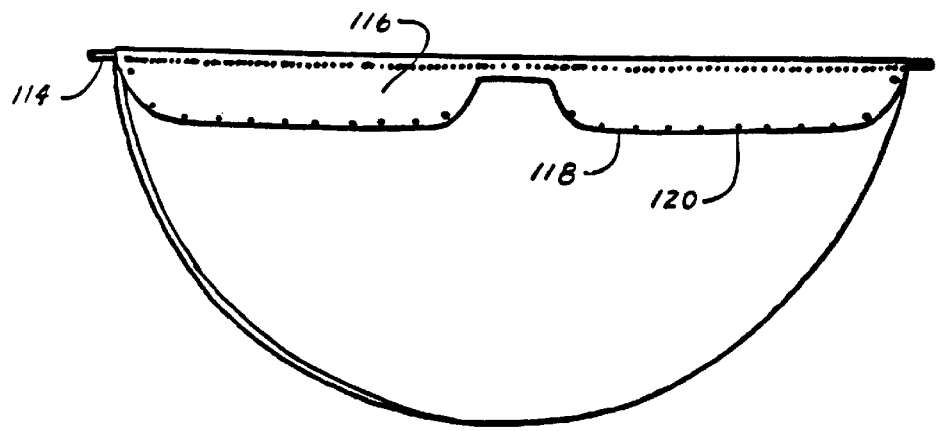
FIG. 11 shows the final laminate sheet, cutting pattern and suture hole pattern for the helical closure device.

FIG. 11 shows the laminate assembly, or membrane 116, high temperature tube 114, outline cutting 118 and suture hole patterns 120. The outline and suture holes are cut by laser, steel rule die, or any other means.

Figure 12:
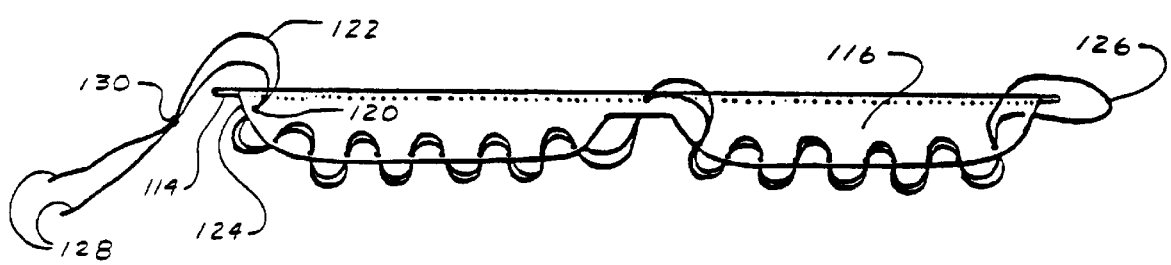
FIG. 12 shows the final laminate with the suture lacing pattern.

FIG. 12 shows a suture threading pattern for the laminated assembly 116. A single suture 122 is threaded from the left edge 124, through the pre-cut holes 120. After the first pass, the suture is folded back upon itself, forming a "bend" 126, and threaded in a reverse pattern through pre-cut holes, returning to the left edge 124. The two suture ends 128 are tied with a single knot 130. The helical wire 112 (FIG. 9(C)), with the FEP coating 30 (FIG. 9(C)), is tensioned into a linear shape and inserted into the high temperature tube 114. The high temperature tube 114 is removed from the laminated assembly 116, leaving the FEP coated wire captured within the laminated assembly. The laminated assembly and the captured wire are then heated to the FEP melting point, reflowing the FEP, which bonds the wire to the ePTFE membrane.

Figure 13:
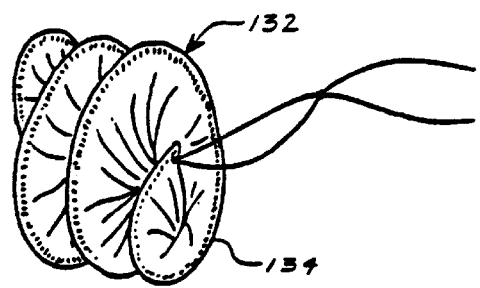
FIG. 13 shows an isometric view of a helical closure device, in the deployed or large diameter state.

FIG. 13 shows the completed helical closure device 132 in the deployed, relaxed or memory induced, large diameter state 134. The ratios of large to small diameters can be substantial, such as between 10:1 to 100:1, as defined by the star shaped configuration, FIGS. 6(A)–(C).

Figure 14:
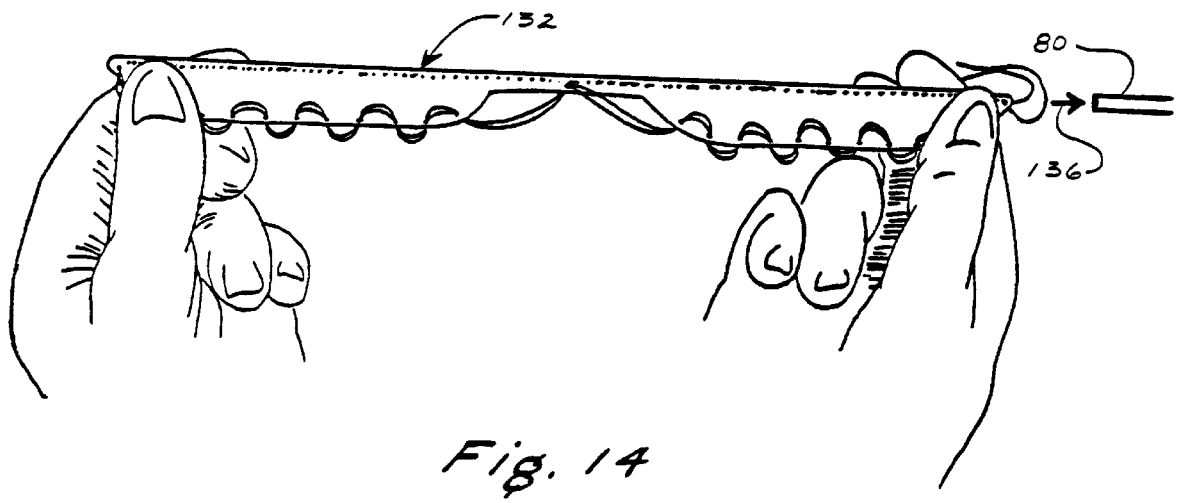
FIG. 14 shows the final device being uncurled and tensioned into a straight profile.

FIG. 14 shows the completed helical closure device 132 being drawn into a linear shape. Once in the linear state, the device can be inserted along the longitudinal axis 136 into a delivery tube 80.

Figure 15A:
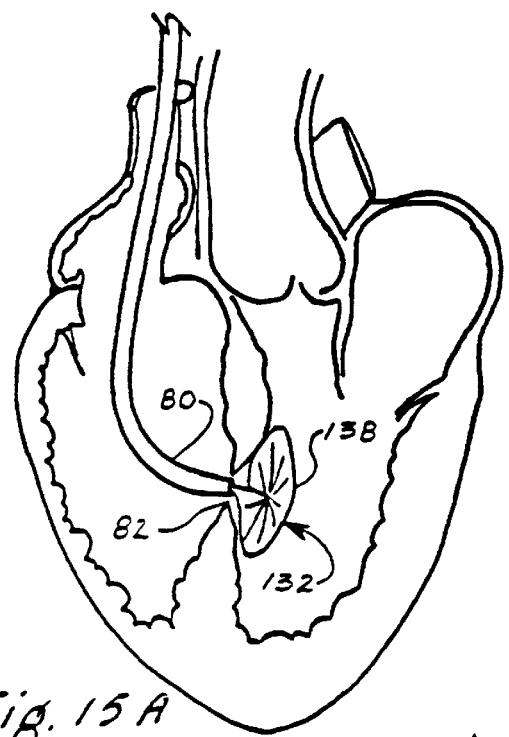
FIG. 15 (A)–(C) show a helical defect closure device according to the present invention being positioned and deployed in a heart defect.
Figure 15B:
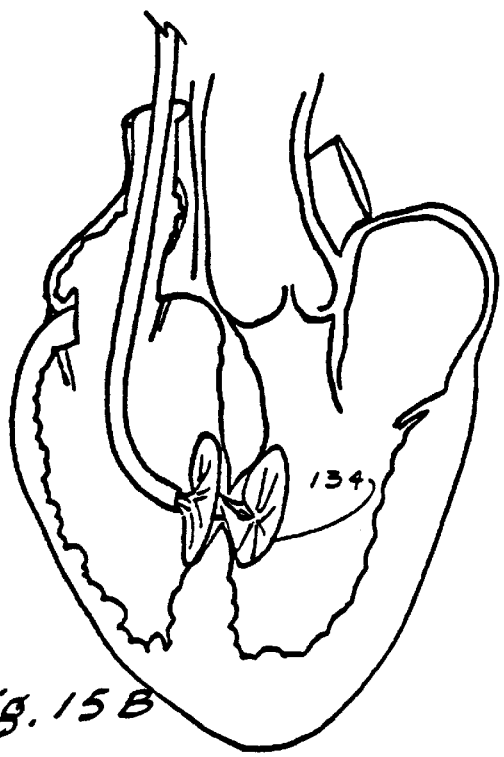
Figure 15C:
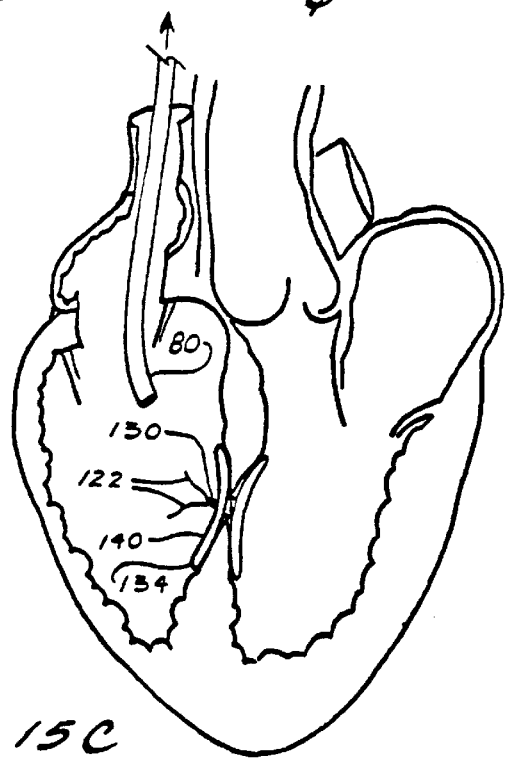

FIGS. 15(A)–(C) show the deployment of the helical closure device 132. A catheter, or delivery tube 80, is loaded with closure device 132 and deployed in a defect 82. As seen in FIG. 15(A), the distal side of the helical device 138 expands when released from the catheter 80. As shown in FIG. 15(B), the distal side of the helical device assumes its memory induced shape 134, which approximates $d_1$ of 76 FIG. 6 (A). As shown in FIG. 15(C), as the catheter is further withdrawn, the proximal side of the device 140 is deployed, the suture 122 is drawn tight, the knot 130 secured and the device assumes its memory induced shape 134.

Figure 16:
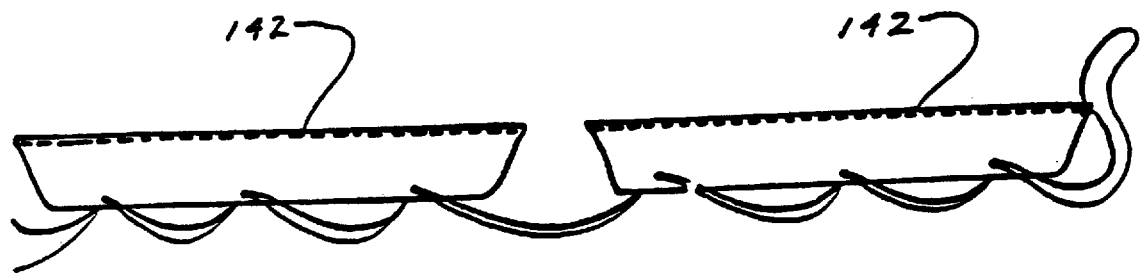
FIG. 16 shows another helical configuration with an adjustable grip feature.
Figure 17:
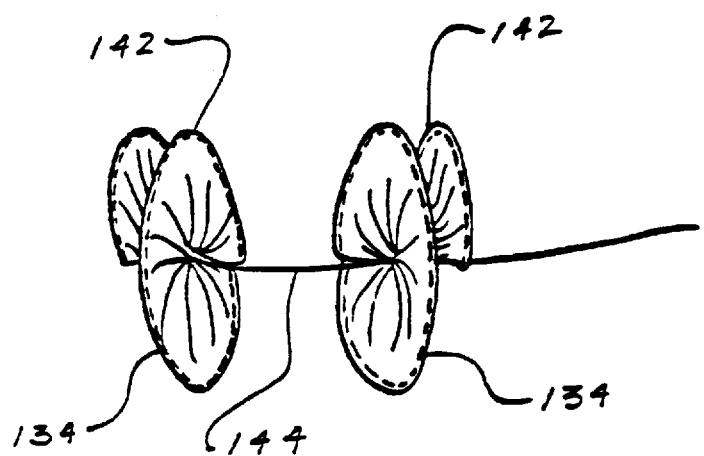
FIG. 17 shows the adjustable grip feature in the deployed or large diameter state.

FIG. 16 shows an alternate helical configuration. The device is fabricated in a process similar to that used for the helical device described above, except the device uses two membrane segments 142, instead of one. The two segments form a relaxed shape 134 as shown in FIG. 17, leaving an adjustable gap 144 between the two membranes 142. This adjustable gap 144 can be used to repair wall defects in a range of wall thicknesses.

Figure 18:
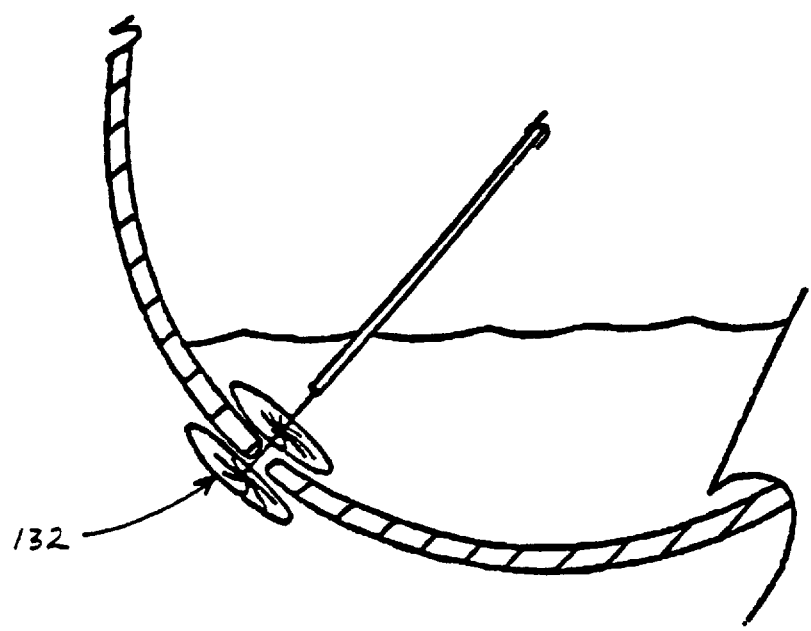
FIG. 18 shows the helical defect closure device positioned in a defect of a container wall.

FIG. 18 shows a vessel wall with a wall defect being sealed by the defect device 132. As seen in FIG. 18, an applicator could be positioned by use of a remote guiding device or be directly employed if conditions allow.

Figure 19A:
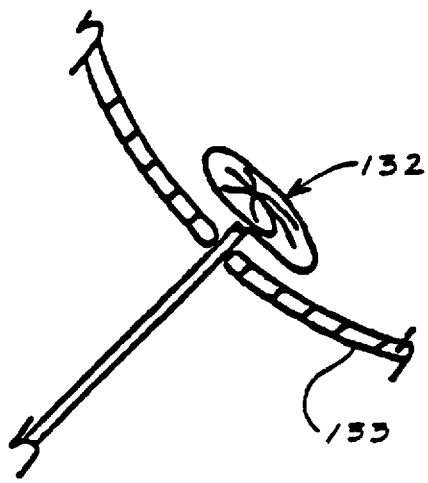
FIGS. 19 (A)–(C) show a helical defect closure device according to the present invention being positioned and deployed in a wall defect.
Figure 19B:
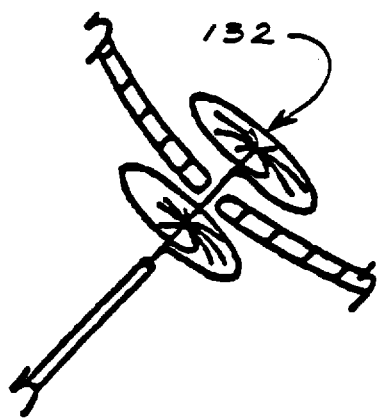
Figure 19C:
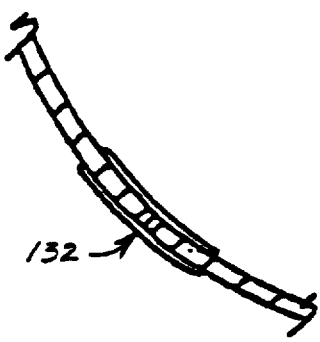

In FIG. 19(A)–(C), the insertion of the closure device 132 into a wall 133 via an applicator is shown following a procedure similar to that described for FIG. 15(A)–(C), except a tube is used.

Figure 20:
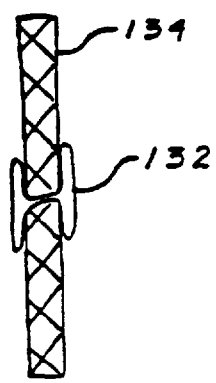
FIG. 20 shows a defect device in a filter medium.

Although FIG. 18 shows the defect closure device of the present invention being employed in a container wall, defects in filters of any design can be repaired by locating the closure device in a tube and deploying it in the defect of filter wall 134 as shown in FIG. 20 following the procedure of FIGS. 19(A)–(C).

Another aspect of the present invention is that a seamless support structure can be constructed by machining a thin sheet of material into the shapes, such as those shown in FIGS. 1 and 8A–8F. In one configuration, 0.203 mm thick Ni—Ti alloy is cut into the profile defined in FIGS. 1 and 8A–8F. A second cut removes the inner area of the structure leaving 0.203 mm width of material at the perimeter. The method of manufacturing the seamless part may be by Electrostatic Discharge Machining (EDM), laser, photo-etch, die cut, or conventional machining. The resultant part is of square cross-section with corners which can be polished down, such as through electro-polishing or abrasive techniques, to achieve rounded corners.

Another variant of the method by which the seamless support structure can be made is slicing sections off of Ni—Ti tube of 0.203 mm wall thickness and with a perimeter equal that of the shape defined in FIGS. 1 and 8A–8F. The thin ring produced using this technique is polished to remove sharp corners and heat treated into the shapes as shown in FIGS. 1 and 8A–8F using a heat treating process.

Although, the present invention is preferred to close body defects like Atrial Septal Defects and Ventricular Septal defects, it can be used in other applications where the undesired communication or passage in the body exists. One specific example is Patent Ductus Arteriosis (PDA). PDA is a vessel which shunts aorta and pulmonary artery. This shunt is supposed to close immediately after childbirth. However, in certain congenital disease conditions, this vessel stays open after childbirth and hence leads to subsequent complications. It is desired to have a catheter based or thoroscopic device to block PDA. The present invention can be used for the PDA closure. Similarly, it can be used to block the flow in any tubular structure in the body such as fallopian tubes, arteriovenous fistula, etc.

In this respect, it should be appreciated that the present invention can be introduced in a wide variety of manners, including by merely using a tube ("catheter"), through thoracoscopic delivery, or other means. For small applications, it may be desirable to use pediatric sized catheters.

Although the invention has been described in conjunction with specific embodiments, it is evident that many alternatives and variations will be apparent to those skilled in the art in light of the foregoing description and annexed drawings. Accordingly, the invention is intended to embrace all of the alternatives and variations that fall within the spirit and scope of the appended claims.

What is claimed is:

1. A self expanding closure device, comprising:
   a) a thin membrane formed from at least one layer of material positionable to have first and second surfaces facing one another and adapted to close a wall defect;
   b) an elastic support attached to said membrane and forming first and second closure portions for said first and second facing surfaces; and
   said elastic support having a first configuration with a longitudinal axis and a diameter of $d_1$ which is compressible into a second, catheter insertable configuration of a diameter $d_2$, where $d_2$ is less than $d_1$, $d_1:d_2$ is between about 5:1 and about 50:1, and said first configuration maintains said closure surfaces in close proximity to the defect.

2. The self-expanding closure device of claim 1, wherein said membrane includes at least two plies of cross-laminated biocompatible material.

3. The self expanding closure device according to claim 2, wherein said membrane is a fluoropolymer.

4. The self expanding closure device according to claim 3, wherein said fluoropolymer is polytetrafluoroethylene.

5. The self expanding closure device according to claim 3, wherein said fluoropolymer is porous, expanded polytetrafluoroethylene.

6. The self-expanding closure device of claim 2, wherein the membrane contains 4–8 plies.

7. The self expanding closure device according to claim 1, wherein said elastic support is a wire.

8. The self expanding closure device according to claim 7, wherein said wire is helically shaped.

9. The self expanding closure device according to claim 8, wherein said helically shaped wire contains at least two complete revolutions about said longitudinal axis.

10. The self expanding closure device according to claim 7, wherein said wire comprises two discrete substantially planer patterns, each of said patterns defining one of said first or second closure portions.

11. The self expanding closure device according to claim 10, wherein each of said patterns is star shaped, where arms of the star radially support said membrane and each of said arms includes first and second legs connected at their distal ends to respective ends of an arcuate connector.

12. The self expanding closure device according to claim 11, wherein said arcuate connector extends over an angle of less than 360°.

13. The self expanding closure device according to claim 7, wherein said wire is nitinol.

14. The self expanding closure device according to claim 7, wherein said wire has shape induced memory.

15. The self expanding closure device according to claim 1, wherein the ratio of $d_1:d_2$ is about 10:1 to about 50:1.

16. A method of assembling a self-expanding defect closure device, comprising:
   a) providing a first membrane portion;
   b) locating an elastic wire on an upper surface of said first membrane portion;
   c) locating a second membrane portion on an exposed surface of said wire of step b) and in contact with said upper surface of said first membrane portion; and
   d) affixing said first and second membrane portions to one another to attach said wire therein.

17. The method according to claim 16, wherein said first and second membrane portions are formed from several plies of material that are cross laminated to one another.

18. The method according to claim 16, wherein said wire is nitinol.

19. The method according to claim 16, wherein said wire has a memory induced shape.

20. The method according to claim 19, wherein configuration is star shaped or helical.

21. The method according to claim 16, wherein said first and second membrane portions are a fluoropolymer.

22. The method according to claim 21, wherein said fluoropolymer is polytetrafluoroethylene.

23. The method according to claim 21, wherein said fluoropolymer is expanded polytetrafluoroethylene.

24. A self expanding defect closure device made in accordance with the method of claim 16.

25. The self expanding defect closure device according to claim 24, wherein said first and second membranes are formed from several plies of material that are cross-laminated to one another.

26. The self expanding defect closure device according to claim 24, wherein said wire is nitinol.

27. The self expanding defect closure device according to claim 24, wherein said wire has a memory induced configuration.

28. The self expanding defect closure device according to claim 27, wherein the configuration is star shaped.

29. The self expanding defect closure device according to claim 24, wherein said first and second membranes are a fluoropolymer.

30. The self expanding defect closure device according to claim 29, wherein said fluoropolymer is polytetrafluoroethylene.

31. The self expanding closure device according to claim 29, wherein said fluoropolymer is expanded polytetrafluoroethylene.

32. A method of closing a defect in a living animal, comprising,
   a) providing a 9F or smaller catheter;
   b) compressing and inserting the device of claim 1 into said catheter;
   c) deploying said compressed device in a defect; and
   d) inserting and releasing said device in said defect.

33. A method of closing a defect in a living animal, comprising,
   a) providing a 5F or smaller catheter;
   b) compressing and inserting the device of claim 1 into said catheter;
   c) deploying said compressed device in a defect; and
   d) inserting and releasing said device in said defect.

34. A method of closing a defect in a living animal, comprising,
   a) providing thoracoscopic delivery system;
   b) compressing and inserting the device of claim 1 into said thoracoscopic delivery system;
   c) deploying said compressed device in a defect; and
   d) inserting and releasing said device in said defect.

35. A method of closing a defect in a container wall, comprising,
   a) providing a delivery tube;
   b) compressing and inserting the device of claim 1 into said tube;
   c) deploying said compressed device in a defect of a container wall; and
   d) inserting and releasing said device in said defect in said container wall.

36. A method of closing a defect in a filter medium, comprising,
   a) providing a delivery tube;
   b) compressing and inserting the device of claim 1 into said tube;
   c) deploying said compressed device in a defect of a filter medium; and
   d) inserting and releasing said device in said defect in said filter medium.

37. A method of assembling a self-expanding defect closure device, comprising:
   a) providing a membrane;
   b) locating a heat resistant tube on said membrane;
   c) folding and laminating said membrane about said heat resistant tube;
   d) inserting an elastic wire into said heat resistant tube; and
   e) removing said heat resistant tube and heating said membrane to embed said elastic wire.

38. The method according to claim 37, wherein said membrane is formed from several plies of material that are cross-laminated to one another.

39. The method according to claim 37, wherein said wire is nitinol.

40. The method according to claim 37, wherein said wire has a memory induced configuration.

41. The method according to claim 37, wherein said wire has a memory induced helical configuration.

42. The method according to claim 37, wherein said membrane is a fluoropolymer.

43. The method according to claim 42, wherein said fluoropolymer is polytetrafluoroethylene.

44. The method according to claim 42, wherein said fluoropolymer is expanded polytetrafluoroethylene.

45. A self expanding closure device, comprising:
   a) a thin membrane formed from at least two plies of cross-laminated biocompatible materials positionable to have first and second surfaces facing one another and adapted to close a wall defect;
   b) an elastic support attached to said membrane and forming first and second closure portions for said first and second facing surfaces; and said elastic support having a first configuration with a longitudinal axis and a diameter of d1 which is compressible into a second, catheter insertable configuration of a diameter d2, where d2 is less than d1, d1:d2 is between about 5:1 and about 50:1, and first configuration maintains said closure surfaces in close proximity to the defect.

46. The self expanding closure device according to claim 45, wherein said elastic support is a wire.

47. The self expanding closure device according to claim 46, wherein said wire is helically shaped.

48. The self expanding closure device according to claim 47, wherein said helically shaped wire contains at least two complete revolutions about said longitudinal axis.

49. The self expanding closure device according to claim 46, wherein said wire comprises two discrete substantially planer patterns, each of said patterns defining one of said first or second closure portions.

50. The self expanding closure device according to claim 49, wherein each of said patterns is star shaped, where arms of the star radially support said membrane and each of said arms includes first and second legs connected at their distal ends to respective ends of an arcuate connector.

51. The self expanding closure device according to claim 50, wherein said arcuate connector extends over an angle of less than 360 degrees.

52. The self expanding closure device according to claim 46, wherein said wire is nitinol.

53. The self expanding closure device according to claim 46, wherein said wire has shape induced memory.

54. The self expanding closure device according to claim 45, wherein said membrane is a fluoropolymer.

55. The self expanding closure device according to claim 54, wherein said fluoropolymer is polytetrafluoroethylene.

56. The self expanding closure device according to claim 54, wherein said fluoropolymer is porous, expanded polytetrafluoroethylene.

57. The self expanding closure device of claim 45, wherein the membrane contains 4–8 plies.

58. The self expanding closure device according to claim 45, wherein the ratio of $d_1:d_2$ is about 10:1 to about 50:1.

59. A self expanding closure device, comprising:
   a) a thin membrane formed from at least one layer of material positionable to have first and second surfaces facing one another and adapted to close a wall defect;
   b) an elastic wire attached to said membrane and forming first and second closure portions for said first and second facing surfaces;
   c) said elastic wire comprises two discrete substantially planer star shaped patterns, each of said star shaped patterns defining one of said first or second closure portions, where arms of the star radially support said membrane and each of said arms includes first and second legs connected at their distal ends to respective ends of an arcuate connector; and d) said elastic wire having a first configuration with a longitudinal axis and a diameter of d1 which is compressible into a second, catheter insertable configuration of a diameter d2, where d2 is less than d1, d1:d2 is between about 5:1 and about 50:1, and first configuration maintains said closure surfaces in close proximity to the defect.

60. The self expanding closure device according to claim 59, wherein said arcuate connector extends over an angle of less than 360 degrees.

61. The self expanding closure device according to claim 59, wherein said wire is nitinol.

62. The self expanding closure device according to claim 59, wherein said wire has shape induced memory.

63. The self expanding closure device according to claim 59, wherein said membrane is a fluoropolymer.

64. The self expanding closure device according to claim 63, wherein said fluoropolymer is polytetrafluoroethylene.

65. The self expanding closure device according to claim 63, wherein said fluoropolymer is porous, expanded polytetrafluoroethylene.

66. The self expanding closure device of claim 59, wherein the membrane contains 4–8 layers.

67. The self expanding closure device according to claim 72, wherein the ratio of $d_1:d_2$ is about 10:1 to about 50:1.

68. A self expanding defect closure device, comprising:
a) a first membrane portion having an upper surface;
b) an elastic wire contacting the upper surface of the first membrane portion;
c) a second membrane portion contacting the elastic wire and the upper surface of the first membrane portion; and
d) a means for affixing said first and second membrane portions to one another to attach said wire therein.

69. The self expanding defect closure device according to claim 68, wherein said first and second membranes are formed from at least two plies of material that are cross-laminated together.

70. The self expanding defect closure device according to claim 68, wherein said wire is nitinol.

71. The self expanding defect closure device according to claim 68, wherein said wire has a memory induced configuration.

72. The self expanding defect closure device according to claim 71, wherein the configuration is star shaped.

73. The self expanding defect closure device according to claim 68, wherein said first and second membranes are a fluoropolymer.

74. The self expanding defect closure device according to claim 73, wherein said fluoropolymer is polytetrafluoroethylene.

75. The self expanding closure device according to claim 73, wherein said fluoropolymer is expanded polytetrafluoroethylene.

* * * * *